US00PP36664P2

(12) United States Plant Patent
Cain et al.

(10) Patent No.: US PP36,664 P2
(45) Date of Patent: May 13, 2025

(54) GRAPEVINE PLANT NAMED 'BLOMG05'

(50) Latin Name: ***Vitis vinifera* interspecies hybrid**
Varietal Denomination: BLOMG05

(71) Applicant: BLOOM FRESH INTERNATIONAL LIMITED, London (GB)

(72) Inventors: David Cain, Lutz, FL (US); Christopher Owens, Bakersfield, CA (US)

(73) Assignee: BLOOM FRESH INTERNATIONAL LIMITED, London (GB)

( * ) Notice: Subject to any disclaimer, the term of this patent is extended or adjusted under 35 U.S.C. 154(b) by 0 days.

(21) Appl. No.: 18/951,196

(22) Filed: Nov. 18, 2024

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

(56) References Cited

U.S. PATENT DOCUMENTS

PP26,121 P3 11/2015 Cain
PP28,956 P2 2/2018 Cain

OTHER PUBLICATIONS

U.S. Appl. No. 19/053,502, filed Feb. 14, 2025, by Cain et al. (Not submitted herewith pursuant to the waiver of 37 C.F. R. § 1.98(a)(2)(iii) issued by the Office on Oct. 19, 2004).

*Primary Examiner* — Susan McCormick Ewoldt
(74) *Attorney, Agent, or Firm* — Michael Best & Friedrich LLP

(57) ABSTRACT

'BLOMG05' is a new and distinct grapevine variety characterized by producing medium sized broadly ellipsoid red berries having very crisp texture with a with a strong fruity flavor combining characteristics of muscat and labrusca which ripens in mid-season. Berries are borne on medium size clusters which are loose and do not need gibberellin applications to thin clusters. Gibberellin is required to increase berry size.

1 Drawing Sheet

Latin name of the genus and species: *Vitis vinifera* interspecies hybrid.

Variety denomination: 'BLOMG05'.

BACKGROUND

Described herein is a new and distinct grapevine plant that originated from a hand pollinated cross of 'IFG Nineteen' (U.S. Plant Pat. No. 26,121) and 06156-071-205 (an unpatented, unreleased numbered selection) hybridized in May 2014. The abortive seed traces were subsequently embryo cultured, and the resulting 72 seedlings were planted in the field in April 2015. The present variety of grapevine was selected as a single plant in August 2017 and was asexually propagated by hardwood cuttings grafted on Freedom (unpatented virus free rootstock) in December 2017, near Delano, Kern County, California. These resulting propagules were planted during April 2018 near Delano, Kern County, California and were found to reproduce true-to-type through at least two generations of asexual propagation.

SUMMARY

The new grapevine plant 'BLOMG05' is characterized by producing medium sized broadly ellipsoid red berries having very crisp texture with a strong fruity flavor combining characteristics of muscat and labrusca. Fruit normally ripens mid-season similar in timing to Thompson Seedless (not patented) in California. Berries are borne on medium size clusters which are loose and do not require gibberellin applications to thin clusters. Gibberellin is required to increase berry size. 'BLOMG05' stores well. Stems remain green and berries retain their crisp texture and strong flavor for up to eight weeks in cold storage. To the inventor's knowledge, the known variety to which the new grapevine variety is most similar is 'IFG Nineteen'. 'BLOMG05' differs from 'IFG Nineteen' by having much crisper berry texture, better color development, and less berry shatter pre-harvest and post-harvest.

'BLOMG05' differs from its maternal parent, 'IFG Nineteen' by producing much crisper textured berries, and by producing more intense red pigmentation than 'IFG Nineteen'. Clusters of 'BLOMG05' are shorter and smaller than 'IFG Nineteen'. It differs from its pollen parent, 06156-071-205 (not patented) by ripening about three to four weeks later, by having smaller natural berry size with no distinct flavor, and by having white berries.

BRIEF DESCRIPTION OF THE DRAWINGS OR PHOTOGRAPHS

The colored photographs illustrate the overall appearance of the 'BLOMG05' plant showing the colors as true as it is reasonably possible to obtain in colored reproductions of this type. Colors in the photographs may differ slightly from the color values cited in the detailed botanical description that accurately describe the colors of the plant described herein. These figures are exemplary and will vary depending on the plant and distinguishing characteristics.

FIG. 1 illustrates 'BLOMG05'. The photograph was taken outdoors with indirect lighting. The left side of the drawing has a mature leaf. A mature fruit cluster is represented in the center of the drawing along with a typical berry in cross section. A young shoot tip can be seen on the right side of the drawing.

DETAILED BOTANICAL DESCRIPTION

Throughout this specification, color names beginning with a small letter signify that the name of that color, as used in common speech, is aptly descriptive. Color names beginning with a capital letter designate values based upon a reprint of The R.H.S. Colour Chart, published in 2016 by The Royal Horticultural Society, London, England.

Throughout this specification, subjective description values conform to those set forth by the International Union for the Protection of New Varieties of Plants (UPOV) publication TG/50/10 "Grapevine *Vitis* L. Guidelines for the Conduct of Tests for Distinctness, Uniformity, and Sustainability" Geneva (2023).

The descriptive matter which follows pertains to 'BLOMG05' plants grown in the vicinity of McFarland, Kern County, California during 2023 and 2024, and is believed to apply to plants of the variety grown under similar conditions of soil and climate elsewhere:

VINE

General:

*Vigor*.—Medium vigor. Under similar climatic and nutritional conditions, the thickness of the trunk and the wood shoots are moderate.

*Density of foliage*.—Dense.

*Productivity*.—Productive, producing about 28 to 29 kg of fruit per vine.

*Resistance/susceptibility to typical pests and disease of Vitis vinifera species*.—Not observed to date.

*Plant hardiness zone*.—Fully hardy in USDA zone 9A (2012). Not tested in other zones.

*Root stock*.—Freedom.

*Training method*.—Typically spur pruned leaving 2 bud spurs.

Trunk:

*Trunk diameter of* 4-*year-old vines at* 30 *cm above the soil line*.—Approximately 2.93 cm.

*Shape*.—Short split.

*Surface texture*.—Medium rough texture.

*Inner bark color*.—Greyed-orange: 166A and 166B.

*Outer bark color*.—Greyed-green: 197C.

SHOOTS

Young shoot:

*Form of tip*.—Wide opened.

*Distribution of anthocyanin coloration of tip*.—Piping (striped).

*Intensity of anthocyanin coloration of tip*.—Medium.

*Density of prostrate hairs of tip*.—Medium to dense.

*Density of erect hairs on tip*.—Absent.

*Color*.—Can be any of the following colors; Yellow-green: 144B, and Greyed Purple 183A.

Woody shoot (mature canes):

*Internode length*.—Medium: About 6.8 cm.

*Width at node*.—About 1.45 cm.

*Cross section*.—Circular.

*Surface*.—Edged.

*Main color*.—The following colors were observed: Greyed-orange: 175B and 165B.

*Density of erect hairs on nodes*.—None or very sparse.

*Density of erect hairs on internodes*.—None or very sparse.

*Axillary shoot vigor at full bloom*.—Medium: Approximately 19.5 cm long.

Flowering shoot:

*Vigor during flowering*.—Moderately vigorous.

*Attitude during flowering on shoots not tied*.—Erect.

*Color*.—Dorsal side of internodes — Yellow-green: 144A.

*Color*.—Ventral side of internodes — Yellow-green: 144A.

*Color*.—Dorsal side of nodes — Yellow-green: 144A.

*Color*.—Ventral side of nodes — Yellow-green: 144A.

*Density of prostrate hairs on nodes*.—Sparse.

*Density of erect hairs on nodes*.—None to very sparse.

*Density of prostrate hairs on internode*.—Very sparse.

*Density of erect hairs on internode*.—Very sparse to sparse.

*Anthocyanin coloration of buds*.—Absent.

Tendrils:

*Distribution on the shoot* (*at full flowering*).—Discontinuous.

*Length of tendril*.—Medium: About 22.1 cm.

*Thickness of tendril* 2 *cm from base*.—About 2 mm.

*Color*.—The following colors were observed: Yellow-green: 145A and Greyed-purple: 187A.

*Form*.—Mostly bifurcated.

*Number of consecutive tendrils*.—2.

LEAVES

Young leaves:

*Color of upper surface of first four distal unfolded leaves*.—Yellow-green: 144A.

*Color of lower surface of young leaves*.—Yellow-green: 144A.

*Average intensity of anthocyanin coloration of six distal leaves prior to flowering*.—Absent.

*Density of prostrate hairs between veins* (*lower surface*).—Very sparse.

*Density of prostrate hairs on veins* (*lower surface*).—Sparse.

*Density of erect hairs between veins* (*lower surface*) .—Absent.

*Density of erect hairs on veins* (*lower surface*).—Dense.

Mature leaves (opposite first cluster):

*Average length*.—About 13.7 cm.

*Average width*.—About 17.0 cm.

*Mature leaf size*.—Large.

*Shape of blade*.—Wedge-shaped.

*Number of lobes*.—5.

*Blade venation*.—Palmate.

*Anthocyanin coloration of main veins on upper side of blade*.—Absent.

*Mature leaf profile*.—Undulate.

*Blistering surface of blade upper surface*.—Medium.

*Leaf blade tip*.—In the horizontal plane of the leaf mid-vein. Does not appear to curve downward.

*Leaf apex*.—Broadly acute.

*Leaf margin*.—Serrate.

*Undulation of margin*.—Medium.
*Undulation of blade between main and lateral veins*.—Overall.
*Shape of teeth*.—Mixture of both sides straight and both sides convex.
*Length of teeth*.—Long, about 6.5 mm.
*Width of teeth*.—About 11.7 mm.
*Ratio length/width of teeth*.—Small.
*Shape of upper lateral sinuses*.—Open.
*Depth of upper lateral sinuses*.—Shallow.
*General shape petiole sinus*.—Closed.
*Shape of base of upper leaf sinuses*.—V-shaped.
*Tooth at petiole sinus*.—Absent.
*Density of prostrate hairs between veins on lower surface of blade*.—Very sparse.
*Density of erect hairs between veins on lower surface of blade*.—Absent.
*Density of prostrate hairs on main veins on lower surface of blade*.—Very sparse to sparse.
*Density of erect hairs on main veins on lower surface of blade*.—Sparse to medium.
*Density of prostrate hairs on main veins on upper surface of blade*.—Very sparse.
*Density of erect hairs on main veins on upper surface of blade*.—Absent.
*Autumn coloration of leaves*.—Leaves can be a single color or combination of colors, in a mottled pattern or on the edges of the leaves. The following colors were observed: Greyed-yellow group 161B and Yellow-orange group 20B.
*Upper surface*.—Color — Green: 137A. Anthocyanin coloration of main veins (upper surface) — Absent. Color of main veins — Yellow-green: 145A. Surface appearance — Semi-glossy. Blistering surface of blade — Medium.
*Lower surface*.—Color — Yellow-green: 144A. Anthocyanin coloration of main veins (lower surface) — Absent. Color of main veins — Yellow-green: 145A. Glossiness — Weak. Surface texture — Rugose. Surface appearance — Dull.

Petiole:
*Length*.—About 13.6 cm.
*Diameter of petiole 2 cm from blade*.—About 3.3 mm.
*Petiole color*.—The following colors were observed: Yellow-green: 145A and Greyed-purple: 187B.
*Length of petiole compared to middle vein*.—Equal.
*Density of prostrate hairs on petiole*.—Sparse.
*Density of erect hairs on petiole*.—Sparse to medium.

Buds:
*Bud fruitfulness*.—Basal: mostly fruitful.
*Position of first fruitful shoot on previous season cane*.—$1^{st}$ to $2^{nd}$ node.
*Dormant bud length*.—About 6.34 mm.
*Dormant bud width in the proximal/distal plane*.—About 4.57 mm.
*Dormant bud color*.—Greyed-orange group N167A.
*Time of bud burst*.—Mid-season: About Mar. 20, 2023.

FLOWERS

General:
*Flower sex*.—Hermaphrodite.
*Length of single flower, unopened*.—About 2.9 mm.
*Width of single flower*.—Unopened: About 1.9 mm. Opened: About 6.3 mm.
*Stamen length*.—About 2.9 mm.
*Stamen count*.—5, occasionally 6.
*Pollen color*.—White: NN155A.
*Pistil length*.—About 3.3 mm.
*Pistil color*.—Yellow-green: 144A.
*Length of first inflorescence*.—Medium: About 23.4 cm long by 9.2 cm wide.
*Position of first flowering and fruiting node*.—$2^{nd}$ to $3^{rd}$ node (current season growth).
*Number of inflorescences per flowering shoot*.—2.
*Time of bloom*.—Midseason as compared with similar varieties in the growing area of McFarland, California.
*Date of full bloom*.—About May 16, 2023.

FRUIT

General:
*Ripening period*.—Medium: Approximately Aug. 12, 2024.
*Use*.—Fresh market.
*Keeping quality*.—Stems remain green, and berries retain their crisp texture and strong flavor for up to eight weeks in cold storage.
*Refractometer test*.—Soluble solids: About 25.3 Brix.
*Brix/acid*.—About 40.32.
*Titratable acidity*.—About 0.62.
*Juice pH*.—About 4.
*Juice color*.—Yellow-green: 145C.

Cluster:
*Mature cluster length (peduncle excluded)*.—About 22.6 cm.
*Mature cluster width*.—About 12.7 cm.
*Mature cluster weight*.—About 573.1 g.
*Bunch density*.—Medium: densely distributed berries, pedicels not visible, berries movable.
*Number of berries*.—About 120.5.
*Form*.—Conical.

Peduncle:
*Lignification of peduncle*.—Weak.
*Diameter of peduncle*.—Approximately 4.20 mm.
*Length of peduncle*.—Short: Approximately 5.73 cm.
*Color of peduncle*.—Yellow-green: 144B.

Berry:
*Uniformity of size*.—Uniform.
*Single berry weight*.—About 6.4 g natural; to about 8.2 g when treated with gibberellic acid.
*Shape*.—Broad ellipsoid.
*Seeds*.—Absent — contains tiny rudimentary seed traces.
*Cross section*.—Circular.
*Berry dimensions*.—Longitudinal axis: about 2.43 cm: Horizontal axis: about 1.83 cm.
*Pedicel length*.—About 6.7 mm.
*Pedicel width*.—About 1.61 mm.
*Pedicel color*.—Yellow-green: 144B.
*Berry firmness*.—Very firm.
*Flavor*.—Strong fruity flavor combining muscat and labrusca.
*Bloom (cuticular wax)*.—Very strong.
*Berry separation from pedicel*.—Medium.
*Skin color (without bloom)*.—Greyed-purple group 187A.
*Flesh color*.—Yellow-green: 144D.
*Anthocyanin color of flesh*.—Absent.

Skin:

*Thickness*.—Medium.

*Skin toughness*.—Somewhat notable when chewing.

*Reticulation*.—Absent.

*Tenacity*.—Tenacious to flesh.

What is claimed is:

1. A new and distinct variety of grapevine plant named 'BLOMG05' as substantially described and illustrated herein.

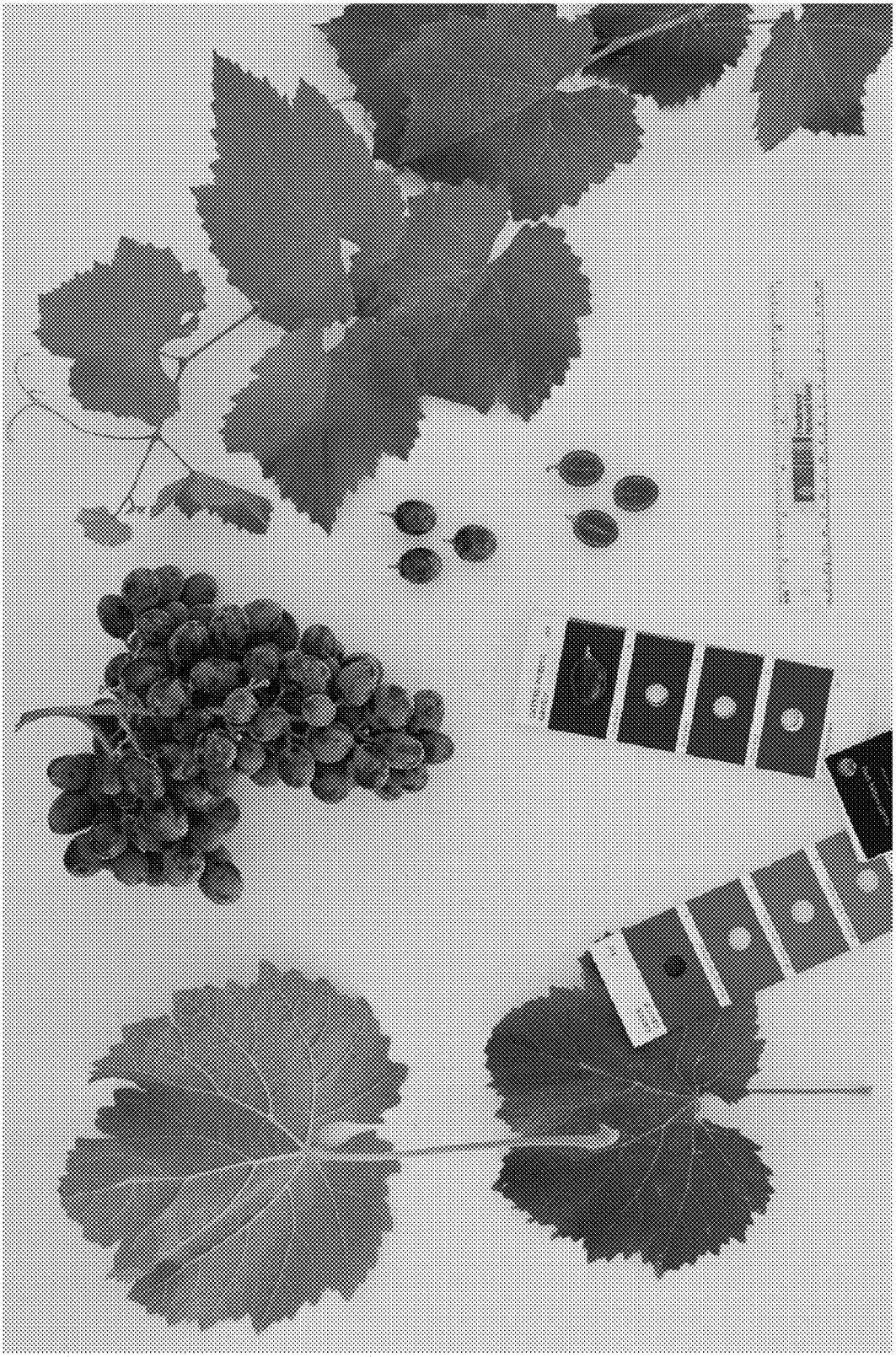

* * * * *